United States Patent [19]

Labaere

[11] Patent Number: 5,193,529
[45] Date of Patent: Mar. 16, 1993

[54] APPLICANCE FOR USE IN INSPIRATION AND EXPIRATION TECHNIQUES AND EXERCISES

[76] Inventor: Emmanuel Labaere, Bruggestraat 133, B-8600 Menen, Belgium

[21] Appl. No.: 562,573

[22] Filed: Aug. 3, 1990

[30] Foreign Application Priority Data

Aug. 3, 1989 [BE] Belgium .............................. 8900839

[51] Int. Cl.$^5$ ..................... A63B 23/00; A61M 15/00; A62B 7/00
[52] U.S. Cl. ................................ 128/200.24; 482/13
[58] Field of Search ...................... 128/200.24, 207.14, 128/207.16, 914; 272/99; 482/13

[56] References Cited

U.S. PATENT DOCUMENTS

| 3,908,987 | 9/1975 | Boehringer | 272/99 |
| 4,210,137 | 7/1980 | Henkin | 128/200.24 |
| 4,231,375 | 11/1980 | Boehringer et al. | 128/725 |
| 4,275,722 | 6/1981 | Sorenson | 128/200.24 |
| 4,478,215 | 10/1984 | Hanlon | 128/207.14 |
| 4,854,574 | 8/1989 | Larson et al. | 128/200.24 |
| 5,018,517 | 5/1991 | Liardet | 128/200.24 |
| 5,027,809 | 7/1991 | Robinson | 128/203.24 |

FOREIGN PATENT DOCUMENTS

3624643 1/1988 Fed. Rep. of Germany.
89/03707 5/1989 PCT Int'l Appl..

Primary Examiner—Edgar S. Burr
Assistant Examiner—Kimberly L. Asher
Attorney, Agent, or Firm—James Creighton Wray

[57] ABSTRACT

Appliance for the application of inspiration and expiration techniques, comprising an elongated cylindrical base part which is passed through by a channel, in which the patient has to breathe through a hollow pipe with mouthpiece, on the one hand, a device being provided which causes a periodically alternating expiration pressure with changeable course during the same exhalation and, on the other, in conjunction therewith, provision being made for a regulating device by which the inspiration and expiration pressure can be regulated infinitely variably at any moment.

7 Claims, 5 Drawing Sheets fig 4a   fig 4b fig 5a   fig 5b fig 6a   fig 6b   fig 6c fig 6d   fig 6e fig 8 fig 7a fig 7b fig 9

APPLIANCE FOR USE IN INSPIRATION AND EXPIRATION TECHNIQUES AND EXERCISES

BACKGROUND OF THE INVENTION

In the treatment of patients with lung problems or with the air passages in general, certain respiration techniques are often used to improve their state of health. These concern more specific treatments of patients with acute or chronic obstructive lung disorders, such as coughing, bronchitis, asthma, emphysema, mucoviscidosis etc...., or with acute or chronic restrictive lung disorders such as pneumoconiosis, or also treatments to improve lung and breathing capacity.

Specific inspiration and/or expiration techniques exist for each of these treatments. A first technique, called "positive expiration pressure" (PEP) involves making the patient exhale against increased resistance by making use of a tube with a narrowed opening, as a result of which the air passages are kept open by an increased intrabronchial pressure during expiration. This technique is often used with the aid of an anesthesia mask on which a T-shaped attachment with inspiration and expiration opening is provided on the breathing opening. Through the fact that various attachments with different narrowed openings can be pushed onto the expiration opening, with this appliance the patient can be made to exhale at different expiration pressures, depending on the required treatment. This appliance has various disadvantages: namely that the resistance, and thus the expiration pressure, cannot be adjusted during one and the same expiration. This means that a wrongly selected attachment (too narrow an opening) could cause the patient breathing difficulties. Another factor is that the appliance is difficult to clean, and is relatively expensive in relation to its facilities.

A second, commonly used technique, "intermittent positive expiration pressure", involves making the patient exhale against a varying resistance by interrupting the expiration flow and permitting it again in rapid alternation according to a periodically alternating pattern. This technique is applied by making the patient exhale into a small appliance which has a round ball of light material on the tube opening in the head which widens out vertically like a smoking pipe. Through the expiration this ball carries out upward and downward movements in rapid succession, through the interaction between the expiration pressure (which varies according to the position of the ball) and the force of gravity which, of course, remains constant. The expiration air is thereby interrupted and allowed through intermittently. The object of this technique is to cause vibrations in the air passages, as a result of which excess mucous breaks up, or to increase the overall lung capacity.

The disadvantages of these types of appliances, as they are currently being put on the market, are that they are impractical in use because they cannot be used with the patient lying down (the head must be used vertically), and that they do not permit any variations in the vibration pattern of the ball, or in the expiration resistance, since it is always the same ball which is used, and the expiration opening is not made adjustable. It goes without saying that this fixed expiration resistance cannot be optimum for all patients (e.g. children). Besides, these appliances are very expensive considering their limited facilities.

Another technique which could be applied, and for which no specific appliances are available on the market, involves inspiration against increased resistance, known as "vario orifice inspiration" or "incentive inspiration", the object of which is to bring about a restoration in the balance between the $O_2$ and the $CO_2$ tension in the body, which is necessary, for example, in the case of hyperoxygenation syndromes (better known as hyperventilation).

SUMMARY OF THE INVENTION

The subject of the invention is an appliance for the application of various inspiration and expiration techniques.

The object of the invention is in the first instance to make the above-mentioned inspiration and expiration techniques applicable with the aid of one and the same appliance, by which the cost, bearing in mind the facilities, becomes far lower than is the case with the currently existing appliances.

Another object of the invention is to eliminate the above-mentioned disadvantages of the individual existing appliances.

The appliance according to the invention comprises a base part, provided with a handgrip at one of the ends, characterized in that this part is provided internally with a tubular channel which runs through the above-mentioned part, and at the level of one outlet provision is made to extend the said channel to the outside by connecting thereto in a rotatable manner a hollow pipe with mouthpiece, and at the level of the other outlet of said channel, connected thereto, is a device which forms a connection of the channel to the outside, and ensures that during the same expiration in the hollow pipe the air is blocked and allowed through in rapid alternation, while advantage can be taken of the course of the periodically alternating expiration pressure by a regulation, or by replacing specific parts of the device, or by replacing the device itself.

The above-mentioned device for obtaining a variable, periodically alternating expiration pressure essentially comprises an element which as regards shape and dimensions is provided to shut off the flow passage of the air, and which is, on the one hand, acted upon by a constant force (e.g. gravity) which presses the element onto said flow passage (if this force is dominant), and which is, on the other hand, acted upon in the opposite direction by the expiration pressure which produces a variable force on the element depending on the position of the element relative to the flow passage (the less air allowed through, the greater said force at that moment), and which pushes the element away from the flow passage (if this force is dominant).

Through the interaction between these two forces, which are such that each of them dominates in turn (due to the fact that one of them is variable), a periodically rapidly alternating expiration pressure is produced, through the fact that the flow passage is shut off and opened again in rapid succession. The regulation of the course of this periodically alternating expiration pressure takes place through altering the constant force acting upon the element, which is possible for the force of gravity by providing an element of a different weight.

The above-mentioned subject of the invention is further characterized in that engaging in the internal channel is a device with which the resistance encountered by the air flow in the channel can be regulated, or by means of which, more particularly, the passage for the air through this channel can be made regulable, this device being controllable from the outside of the appliance by means of a rotary knob, position switch, handle or similar control device.

Further features and advantages of the appliance for the use of various inspiration and expiration techniques according to the invention will emerge from the description below of two preferred embodiments of the appliance, without the invention being limited to these embodiments. This description is illustrated by the appended figures.

DETAILED DESCRIPTION OF THE DRAWINGS

Figure 8:
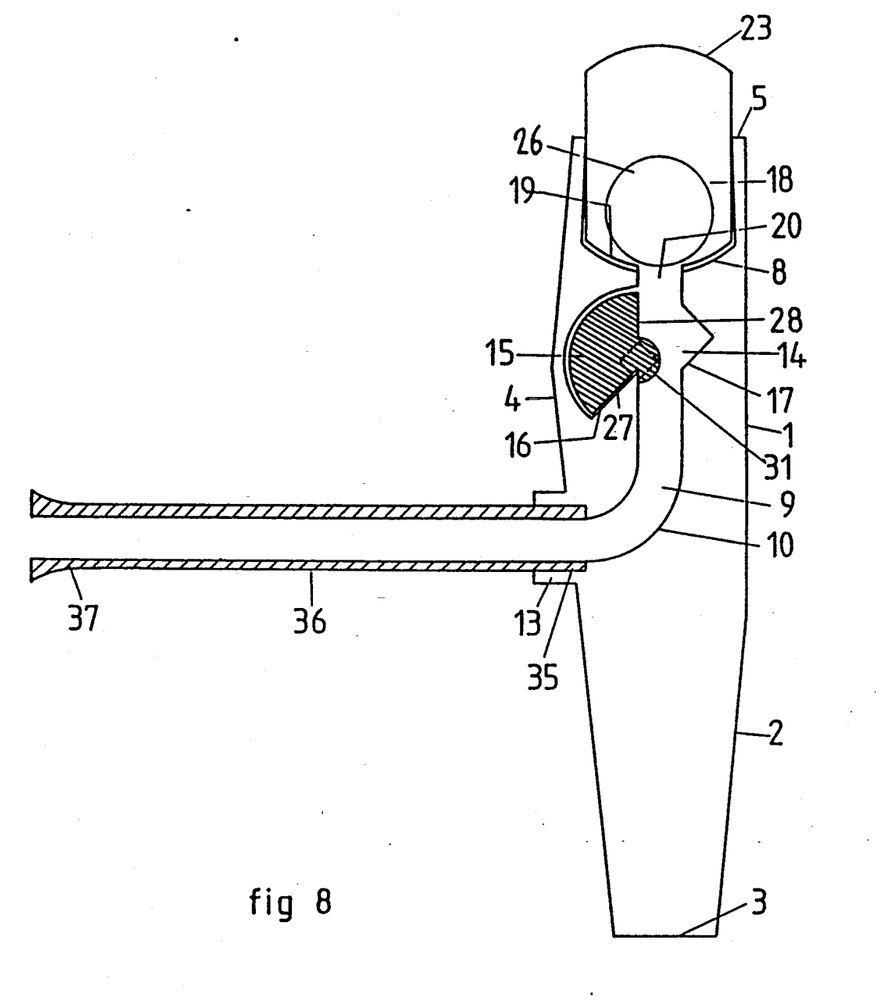
FIG. 8 shows in side view a partial cross-section of the complete appliance, according to a first embodiment of the invention.
Figure 9:
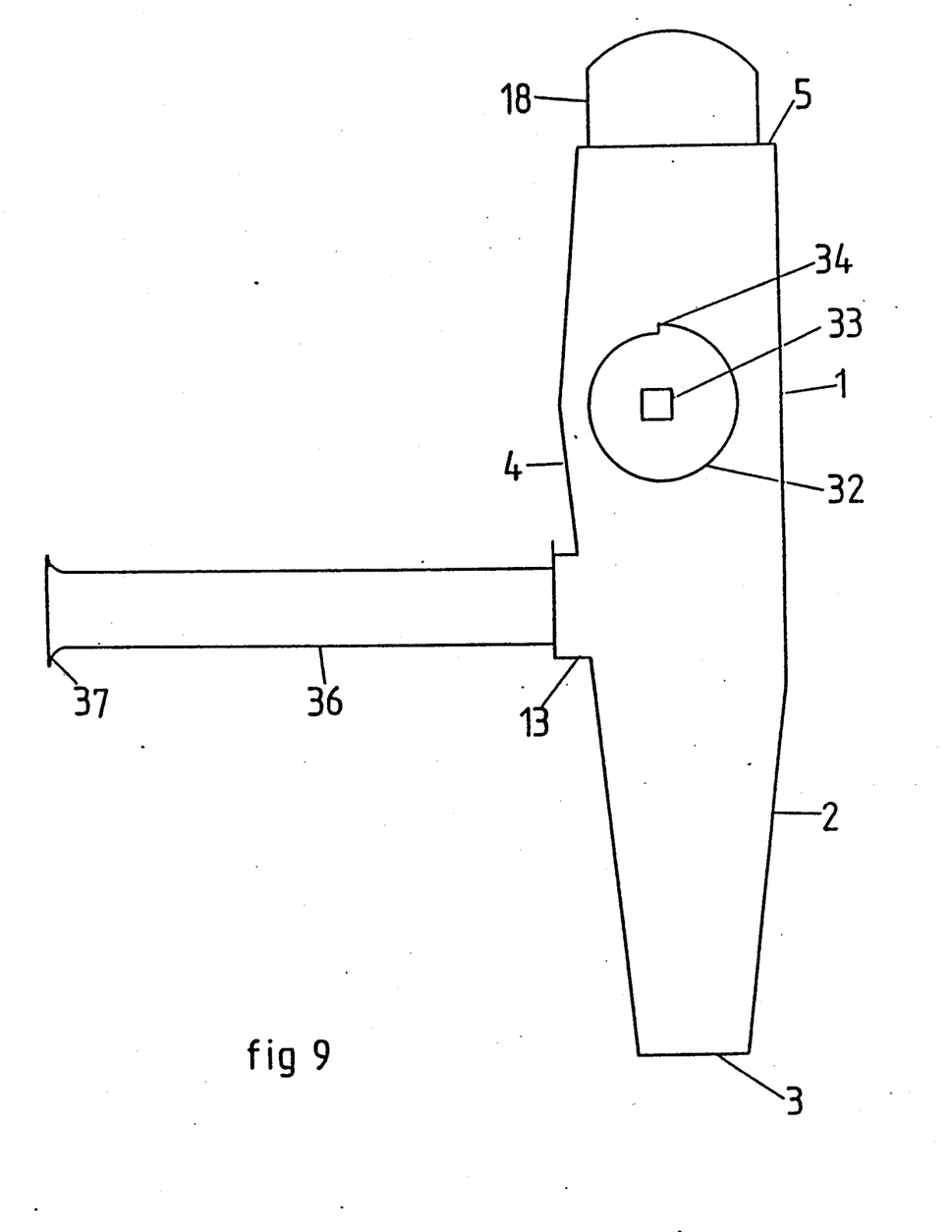
FIG. 9 shows in side view the complete appliance according to a first proposed embodiment of the invention.

The appliance for the application of various inspiration and expiration techniques, according to the invention and according to a first preferred embodiment thereof, shown in its entirety in FIGS. 8 and 9, and shown in individual parts in the figures preceding them, is characterized in that it is made up of an elongated base part (1), with walls rounded off to a circular shape, in which one end (2) of this base part (1) is made tapering towards the end, so that the said base part (1) ends with a circular, flat side (3), and in which the diameters and the taper are selected in such a way that said end (2) with the circular side (3) downwards can serve as a handgrip of the appliance, it being possible for the circumference of the tapering end (2) to be enclosed in one hand of any patient in order to hold the appliance firmly, in the vertical position of the elongated base part (1).

Figure 1A:
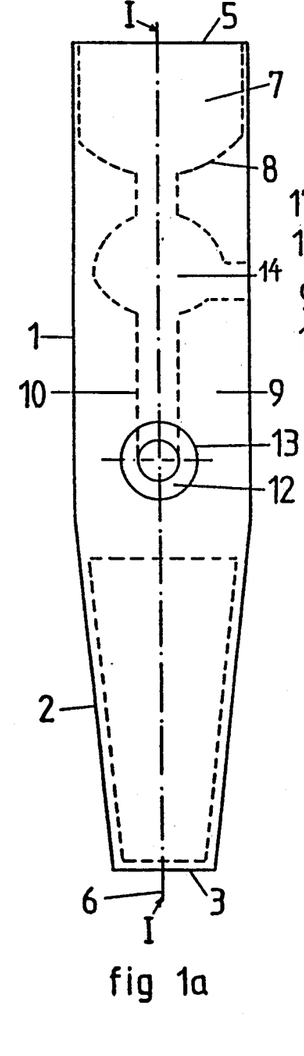
FIGS. 1a and 1b show the base part of an appliance, according to a first embodiment of the invention, in front view and in top view respectively.
Figure 1B:
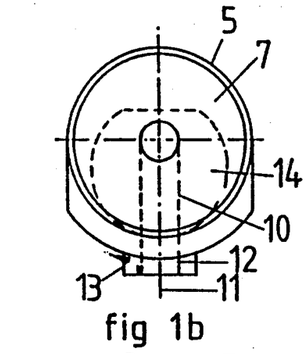
Figure 2A:
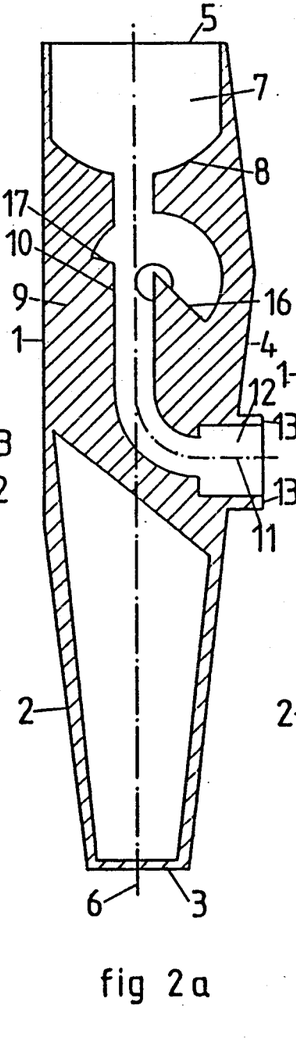
FIGS. 2a and 2b show respectively a cross-section of the base part of the appliance along the axis I—I in FIG. 1a and the top view of this cross-section.
Figure 2B:
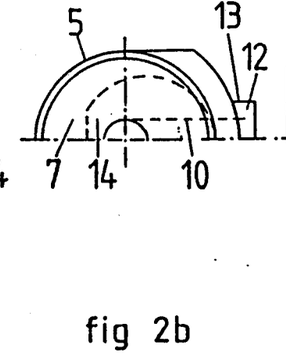
Figure 3A:
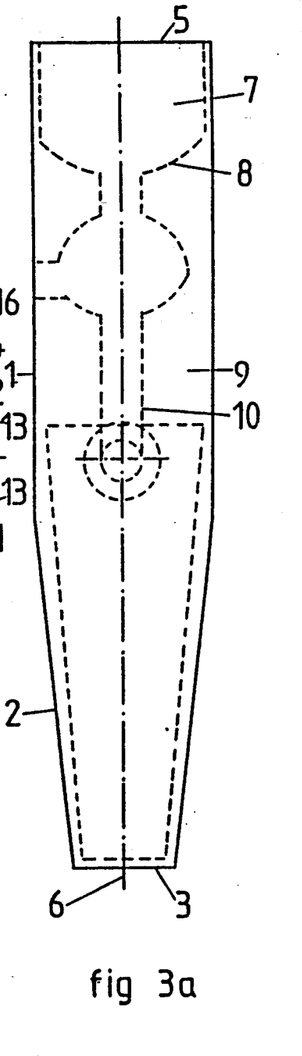
FIGS. 3a and 3b show respectively the rear view and the corresponding top view of the base part of the appliance, in the first embodiment.
Figure 3B:
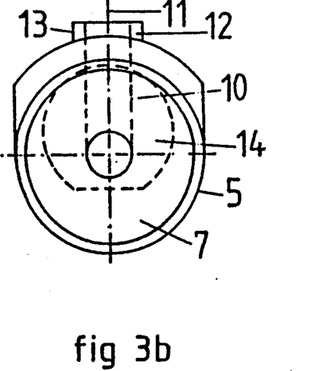

The appliance according to the invention described here is further characterized (FIGS. 1a, 2a, 3a) in that the base part (1), above the bottom tapering end (2), widens out asymmetrically upwards, and closer to the other end narrows again, through a first widening front side (4) (in line with the tapering handgrip (2)), which is then made narrowing again higher up towards the top side (5) of the base part (1), in such a way that the top side (5) of the base part (1) is again circular in cross-section and is symmetrical relative to the axis (6) of the base part (1).

The appliance according to the invention is further characterized in that the circular top side (5) of the base part (1) is provided with a cylindrical recess (7), symmetrical relative to the axis (6) of the appliance, and having a diameter which is slightly smaller than the diameter of the circular top side (5), while the bottom side (8) of the recess (7) is made like a segment of a sphere.

The embodiment of the appliance shown here according to the invention is further characterized in that provision is made internally, passing through a solid part (9) of the base part (1) situated above the tapering handgrip (2), for a tubular channel (10) which at one side opens vertically into the cylindrical recess (7), the axis (11) of the said channel (10) coinciding at that point with the axis (6) of the base part (1), and at the other side after describing a bend of 90° opens horizontally into the front side (4) of the base part (1), the direction of the axis (11) of the channel (10) there lying at right angles to the axis (6) of the base part (1), and the last part (12) of the channel (10) at this outlet describing a cylinder with larger diameter and being extended by a cylindrical edge (13) which forms a projecting part lying beyond the wall surface of the base part (1).

The appliance according to the invention, in the embodiment presented above is also characterized (FIGS. 1a, 2a, 3a and 8) in that the solid part (9) of the base part (1) contains a cavity (14), designed as a widening of the channel (10) in all directions, and the shape of which is provided to contain the regulating part (15) of the device by means of which the passage for the air through the internal channel (10) can be adjusted, the shape of this cavity (14) being a segment of an ellipsoid, obtained by cutting away a piece up to the axis of symmetry in the lengthwise direction, and cutting along two planes of symmetry in the lengthwise direction, with an opening angle of 148° in the transverse plane of symmetry of the ellipsoid, while the above-described cavity (14), on the one hand, is situated in such a way in the solid part (9) of the base part (1) that the extension of the wall of the internal channel (10) lies fully inside the cavity (14) and, on the other hand, is situated in such a way that the axis of symmetry in the lengthwise direction of the original ellipsoid is a horizontal tangent of the walls of the internal channel (10), along the outlet side of the channel in the side of the appliance, and lies in a direction at right angles to the axis (1) of said outlet, while the transverse vertical plane of symmetry of the ellipsoid segment contains the axis (6) of the base part (1), and the cut faces of the segment lie in such a way that one cut face (15) forms an angle of 45° below the horizontal plane through the axis of symmetry in the lengthwise direction of the ellipsoid, along the front side (the outlet side of the channel (10) in the wall (4) of the base part (1)), and that the other cut face (17) forms an angle of 13° above the horizontal plane through the axis of symmetry in the lengthwise direction of the ellipsoid along the rear side of the base part (1).

The appliance according to the proposed embodiment of the invention is further characterized (FIGS. 6a, 6b, 6c, 6d, 6e and 8) in that provided as separate parts are at least two, preferably 5 or more, interchangeable cups (18) with lids (23) which viewed as a whole (cups (18)+lids (23)) have cylindrical sides, and are higher than the depth of the recess (7) in the top side (5) of the base part (1), and have a bottom side (19) which is designed like a segment of a sphere, the shape and the dimensions of the outside of the cups (18), including the lids (23), being such that they are easy to slide bottom side (19) forward into the recess (7), over the full depth thereof, and such that the cylindrical side walls of the cups (18) provided with lids (23) and their bottom side (19) formed as a segment of a sphere abut tightly against respectively the side walls of the recess (7) and the bottom side (8) thereof made in the form of a segment of a sphere, over the full surface of the above-mentioned abutting walls and bottom sides.

The appliance according to the invention is further characterized in that the bottom side (19) of the cups (18) contains an aperture 20, symmetrical relative to the axis of symmetry of the cups, and thus also relative to the axis (6) of the base part (1) (with the cup (18) pushed into the recess (7)), and with a diameter at least equal to the diameter of the outlet aperture of the internal channel (10) which opens vertically into the bottom side (8) of the recess (7). This aperture (20) is situated precisely above the outlet aperture of the channel (10) when the cup (18) is sitting in the recess (7).

The appliance according to the invention is further characterized in that the cups (18) have at the top side of their side wall a symmetrical, recessed part (22), over which the side wall (22") of the cylindrically designed lid (23) fits tightly, designed in such a way that the outside of the side wall (22") of the lid (23) lies in line with the outside of the side wall (22') of the cup (18), and in which the top side (24) of the lid (23) is made in the form of a segment of a sphere and is provided with at least one aperture (25) to the outside, the combined surface area of which is at least equal to the surface area of the outlet aperture of the channel (10).

The appliance according to the invention is also characterized in that the cups (18), provided with lids (23), contain a ball (26) which is spherical with a diameter greater than the diameter of the aperture (20) in the bottom side (19) of the cups (18) and is smaller than the internal diameter of the cylinder shape of the side walls (22) of the cups (18), the weight of the ball (26) being such that when it is at the bottom of the cup (18) and shuts off the outlet aperture of the channel (10) it can be raised through the pressure occurring as a result of an expiration in the channel (10) and clears the outlet aperture of the channel (10), while the weight of the balls (26) in the various cups (10), which are provided for one appliance, according to the invention varies.

Figure 4A:
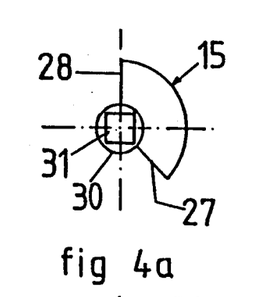
FIGS. 4a and 4b show respectively a side view and a front view of the regulating part of the device, with which the passage for the air through the internal channel of the appliance according to the invention can be regulated, according to a first possible embodiment thereof.
Figure 4B:
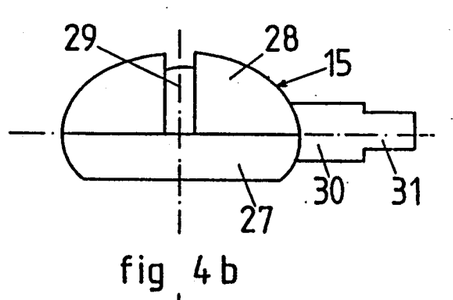

The appliance according to the invention is further characterized in that the above-mentioned cavity (14) which widens the channel (10) in the solid part (9) of the base part (1) contains a regulating part (15) (FIGS. 4a and 4b), the shape of said part (15) being a segment of an ellipsoid which is identical to that determining the cavity (14), but in which a larger part is cut away up to the axis of symmetry in the lengthwise direction and cutting along two planes of symmetry in the lengthwise direction, in such a way (FIG. 8) that, when one cut face (27) of this regulating part (15) is situated on the cut face (16) of the cavity (14), the other cut face (28) of the regulating part (15) is in a vertical position, parallel to the axis (6) of the base part (1).

The appliance according to the invention is further characterized in that this regulating part (15) contains a groove (29) (FIG. 4b) running from the cut face (28), coinciding with the transverse plane of symmetry of this part (15), and running through in the regulating part (15) over such a distance that, when the cut face (28) of the regulating part (15) lies on the cut face (17) of the cavity (14), the groove (29) no longer forms a connection between the bottom and the top part of the channel (10).

Figure 5A:
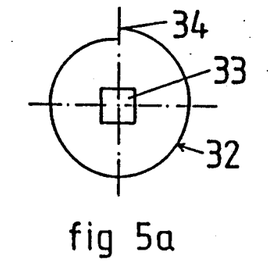
FIGS. 5a and 5b show respectively a front view and a side view of the control knob of the device with which the passage for the air through the internal channel of the appliance according to the invention can be regulated.
Figure 5B:
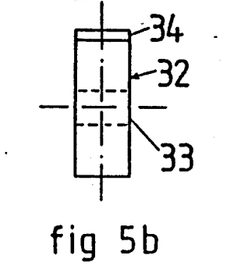
Figure 6A:
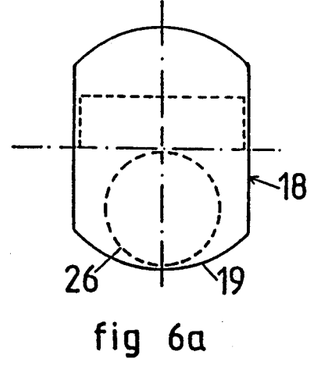
FIGS. 6a, 6b, 6c, 6d and 6e show respectively in side view an exchangeable cup with lid, such a cup without lid, and the lid alone, and a top view and a bottom view of such a cup with its lid for the appliance, according to a first embodiment of the invention.
Figure 6B:
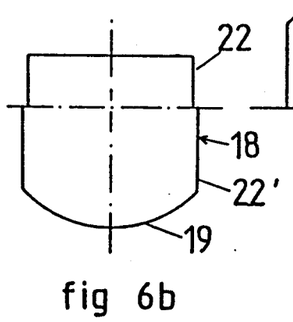
Figure 6C:
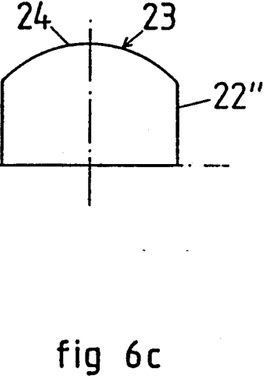
Figure 6D:
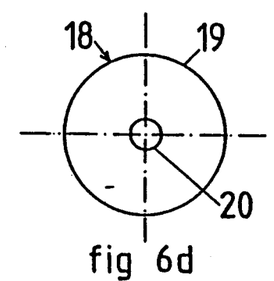
Figure 6E:
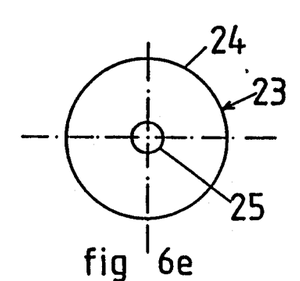

The appliance according to the invention is also characterized (FIGS. 4a and 4b) in that fixed to the regulating part (15), in line with the axis of symmetry in the lengthwise direction of the ellipsoid determining this part, is a cylindrical shaft (30) which projects out through a hole in the side wall of the base part (1), and projects far enough to permit a disc-shaped rotary knob (32) to be pushed over the end (31) with square cross-section of the shaft (30) (FIGS. 5a and 5b), in the center of which knob is a square hole (33) with identical dimensions to those of the shaft end (31), while the side wall of said rotary knob (32) is provided at one point with a tooth form (34) as a marking to determine the position of the rotary knob (32) and the regulating part (15) driven by it.

Figure 7A:
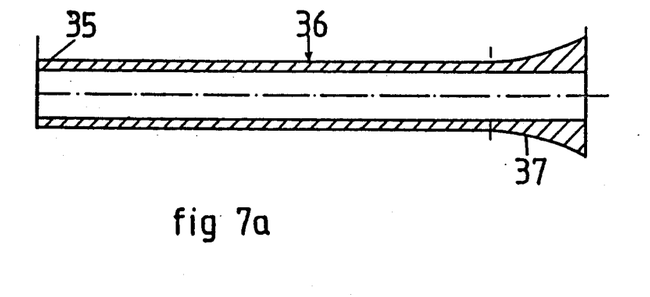
FIGS. 7a and 7b show respectively a longitudinal section and a front view of the hollow pipe for the appliance according to the invention.
Figure 7B:
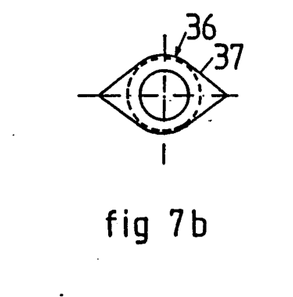

The appliance according to the invention is also characterized in that it is possible to slide into the part (12) with larger diameter of the internal channel (10), at the level of the outlet of said channel (10) in the side wall of the base part (1), and inside the cylindrical edge (13), the cylindrical end (35) of a hollow pipe (36) (FIGS. 7a and 7b), the external dimensions of said end (35) being equal to the internal dimensions of the channel part (12) and the space enclosed by the edge (13), so that said pipe (36) fits tightly with its end (35) in the channel part (12) and inside the edge (13) and sits rotatably therein, and said hollow pipe (36) at the other end is provided with a mouthpiece (37), while the internal diameter of the hollow pipe (36) remains equal everywhere, and the shape of the mouthpiece (37) is obtained by changing the wall thickness of the hollow pipe (36), symmetrical relative to two perpendicular, transverse axes of symmetry, in such a way that the transverse section at the end of the mouthpiece approaches the shape of an open mouth.

The use of the appliance according to the invention involves the patient holding the appliance by the tapering handgrip (2) and putting the mouthpiece (37) of the hollow pipe (36) in his mouth in order to apply the various possible inspiration and expiration techniques.

Another possible embodiment of the appliance according to the invention differs from the embodiment described above (FIGS. 10, 11 and 12) in that no cups (18) with lids (23) are provided, but that the ball (26) is placed directly in the recess (7') in the top side (5') of the base part (1'), while a lid (23') which fits precisely with an edge around the circular edge of the top side (5'), so that it sits firmly thereon, is provided, and this lid (23') is provided with at least one opening towards the outside, the combined surface area of which is at least equal to the outlet aperture of the channel (10') in the recess (7').

Figure 10:
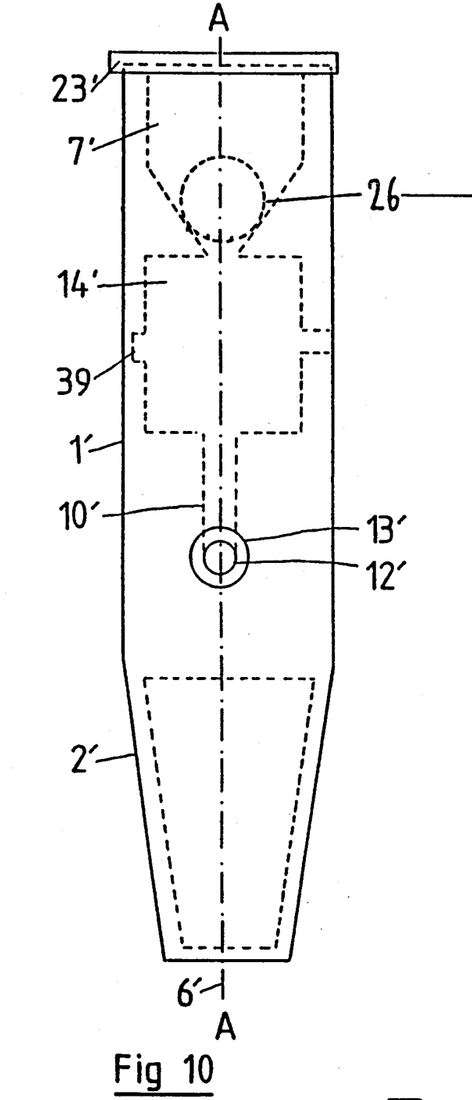
FIG. 10 shows in front view a base part of an appliance, according to a second possible embodiment of the invention.
Figure 11:
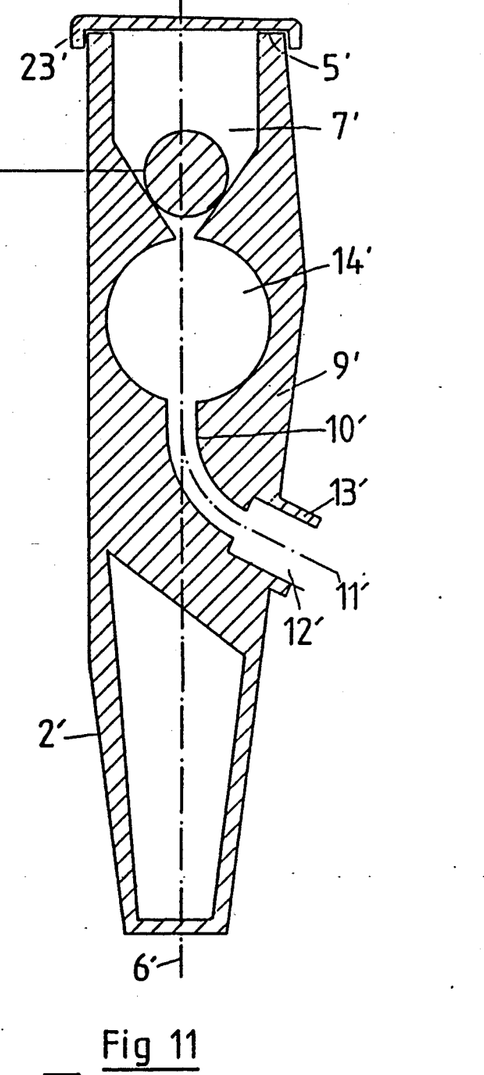
FIG. 11 shows a cross-section of the base part of an appliance along the axis A—A in FIG. 10, and thus according to the second possible embodiment of the invention.

The shape of the recess (7') also differs from the recess (7) described above in that the bottom part tapers towards the outlet of the channel (10'). The device for obtaining periodically alternating expiration pressure for the rest operates the same as that described in detail for the first embodiment, a different alternating pattern for this expiration technique being obtainable in this case by placing a different ball (26) (of greater or smaller weight) in the recess (7').

Figure 12:
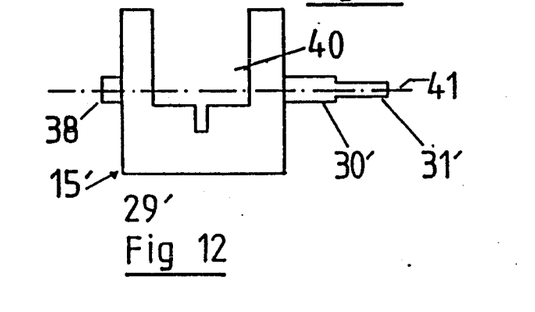
FIG. 12 shows in front view the regulating part of the device by means of which the passage for the air through the internal channel of the appliance can be regulated, according to a second possible embodiment thereof.

Another difference from the first embodiment lies in the design of the cavity (14') and of the regulating part (15'), fitting therein, of the device by means of which the passage for the air through the internal channel (10') can be set. In this embodiment this cavity (14') in the solid part (9') is cylindrical in shape, the axis of symmetry of this cylinder intersecting at right angles and horizontally the axis (6') of the base part (1') and lying in a direction which is at right angles to the axis (11') of the outlet of the channel (10') in the side of the appliance, and this cylinder widening the channel (10') symmetrically. Into this cavity (14') fits a regulating part (15'), of the same cylindrical dimensions, while along one side in line with the axis of symmetry (41) is a projecting cylindrical part (38) which is placed rotatably in a recess (39) (of the same shape and dimensions) in one of the circular side walls of the cavity (14'). Along the other side, in line with said axis of symmetry (41) of the regulating part (15'), is a cylindrical shaft (30') through a hole in the side wall of the base part (1') and provided with a rotary knob (32) on a shaft end (31') of square cross-section, as described above.

This cylindrical regulating part (15') contains a U-shaped recess (40) in the transverse direction, provided at right angles to the axis of symmetry of the cylindrical regulating part (15').

A narrow groove (29'), also U-shaped, and parallel to the above-mentioned recess, is also provided in the center of the flat base of this U-shaped recess (40), in this regulating part (15').

The regulating part (15') described above also makes it possible to regulate the size of the passage infinitely variably by turning the rotary knob (32) which drives the regulating part (15') via the cylindrical shaft (30').

In one extreme position the base of the recess (40) lies parallel to the walls of the channel (10), and thus makes the passage completely free through the recess (40) connecting the top part to the bottom part of the channel (10'). In another extreme position the base of the recess (40) lies at right angles to the walls of the channel, and the regulating part (15') shuts off the flow passage completely, with the cylindrical casing. Within a particular path of the rotary part (15'), in the cavity (14'), only the groove (29') still acts as the flow passage for the air, while the flow passage of this groove is also regulable through rotating the regulating part (15') further, and while for at least one position of the regulating part neither the recess nor the groove forms a connection between the bottom and the top part of the channel (10').

Another difference of this second embodiment according to the invention from the first lies in the fact that the outlet of the internal channel (10') in the wall of the base part (1') does not lie at right angles to the axis (6') of the base part (1'), but is directed downwards at an angle, so that the bend which the channel (10') describes internally is smaller than 90°. The result of this is that the hollow pipe (36) which is pushed inside the edge (13') into the space (12') provided also lies directed downwards, and must be provided with such a mouthpiece (37) that the patient can use the appliance in its vertical position.

During the use of the positive expiration pressure and incentive inspiration the patient exhales and inhales respectively in the hollow pipe (36), while during the same inspiration or expiration the passage in the channel (10) or (10') can be regulated infinitely variably, so that the resistance is regulable at any moment, which was not the case with any of the existing appliances. In these techniques no cup (18) is placed, or no ball (26) provided, in the recess (7) or (7') in the top side (5) or (5') of the base part (1) or (1').

The regulation of the resistance is carried out by turning the rotary knob (32), which by means of the cylindrical shaft (30) or (30') drives the regulating part (15) or (15'), which then turns in the cavity (14) or (14'). For the first possible embodiment of this regulating device the following applies: in the one extreme position the cut face (27) of the regulating part (15) comes to rest on the cut face (16) of the cavity (14) (see FIG. 8), so that the flow passage is completely free and the air can flow with little resistance through the channel (10) (cut face (28) vertical), and in the other extreme position the cut face (28) of the regulating part (15) comes to rest on the cut face (17) of the cavity (14), so that the flow aperture of the channel (10) is completely shut off.

For the second possible embodiment of this regulating device the following applies: when the base of the recess (40) is situated parallel to the walls of the channel (10'), the flow aperture is cleared completely, and the air can flow through with little resistance. The device is in a first extreme position. In the other extreme position the flow aperture is shut off by the cylindrical casing of the regulating part (15').

In both cases the flow aperture (and thus the resistance) is thus regulable at any moment between these extreme positions during inhalation and exhalation, while within a particular path of the regulating part (15) or (15') in the cavity (14) or (14') only the groove (29) or (29') now acts as a flow aperture for the air, this flow aperture also being further regulable by turning the regulating part (15) or (15') further.

In this way it is possible to obtain optimum conditions for the use of the expiration techniques for any patient and for any clinical picture.

During the use of the technique, in which the patient is made to exhale against a varying resistance, by interrupting the exhalation flow and restoring it alternately, the appliance according to the invention is used provided with a ball (26) (which may or may not be in a cup (18) with lid (23)). During expiration the air flows along the hollow pipe (36) and the channel (10) or (10'), and the ball (26), which impedes the passage of the air, is pushed up by the expiration pressure which acts on the ball, and which is greater at that moment than the force of gravity acting upon the ball (26). The air flows past the ball (26), and can reach the opening in the lid (23) or (23'), and flow freely outwards. At the moment the pressure on the ball (26) has, however, become much smaller, and the force of gravity is again greater than the upward pressure, as a result of which the ball falls back down, and the flow aperture shuts off, so that the cycle can begin again.

The succession of situations described above is repeated many times in rapid succession, in a continuous cycle, for the entire duration of the expiration, causing the ball (26), as it were, to vibrate up and down in the cup (18) (or the recess (7')).

The expiration resistance thereby runs according to a rapidly varying pattern, which was the purpose of the technique applied.

At the same time, the continuous resistance can also be adjusted by means of the rotary knob (32), according to the principle described above. Moreover, it is also possible, by sliding another cup (18) of which the ball (26) is greater or smaller in weight into the recess (7') (or by placing a ball of a different weight in the recess (7')), to ensure that the necessary expiration pressure for raising the ball (26) is greater or smaller, so that a different alternating pattern of this expiration technique is obtained.

The advantage of the appliance according to the invention is that the different inspiration and expiration techniques which had to be used by different appliances hitherto can now be used by means of the same appliance, which means that the cost in relation to the facilities of the appliance becomes much lower.

Another advantage of the appliance according to the invention is that during one and the same inspiration or expiration the inspiration or expiration resistance can be regulated infinitely variably.

An additional advantage of the appliance according to the invention is that the hollow pipe (36) is fixed rotatably by its end (35) on the outlet aperture of the channel (10) or (10') in the side wall of the base part (1) or (1'), which makes it possible to use this appliance lying down, since the base part can remain vertical, and in particular the cups (18) (or the recesses (7')) with balls (26), on which the force of gravity has to be able to act vertically, simply by turning the hollow pipe (36) in such a way that the mouthpiece (37) is in the correct position for a patient lying down.

Yet another advantage of the appliance is that during the use of the technique, in which the patient has to exhale against a varying resistance, the alternating pattern of this varying resistance can be changed by providing a ball (26) of which the weight differs, while five different balls are preferably provided with each appliance (situated in changeable cups (18) or otherwise), each of a different weight, while, by way of example, it can be said that these weights are equally distributed between 15 and 40 grammes.

I claim:

1. Inspiration and expiration apparatus for performing positive expiration pressure (PEP), pursed lips breathing (PLB), oscillating positive expiration pressure (OPEP), incentive inspiration (II) and incentive expiration (IE), comprising a handle, a hollow pipe and a channel connectable to a mouthpiece through said hollow pipe and means for periodically alternating expiration pressure with changeable course and, means for infinitely variably regulating inspiration or expiration pressure, wherein the means for periodically alternating expiration pressure comprises an element for shutting off a flow passage for the air through the channel, said element being acted on by a force of gravity in the direction of the flow passage and being acted on in an opposite direction by expiration pressure, said expiration pressure depending on the supply of air allowed through thereby being variable, said expiration pressure resulting in an up and down movement of the element so that the flow passage is shut off and re-opened in rapid succession during the same exhalation, and means for changing the course of the periodically alternating expiration pressure thus obtained, said changing means comprising the changing of the element and weight of the element and thus the force exhaled against.

2. The apparatus of claim 1, comprising an elongated, cylindrical base part, a bottom end being tapered to form a handgrip, and a top end being provided with a symmetrical, cylindrical recess with a centrally situated lowest point, and wherein the channel runs through a solid part of said base part and is tubular, the channel at one side opening out vertically into a lowest point of the cylindrical recess, and at another side opening out into a side wall, not necessarily horizontally, with a cylindrical widening and a projecting edge running through further as a prolongation to receive a cylindrical end of a hollow pipe having a mouthpiece on an opposite end.

3. The apparatus of claim 2, wherein the means for periodically alternating pressure comprises at least two spherical balls of light material, each of a different weight, one of said balls being placed in the recess in the base part, while this recess is shut off by a lid provided with an aperture which is at least as large as an outlet aperture on the channel in the recess, and where each ball, lying on the bottom of the recess, is capable of shutting off the flow passage for the air and is of such weight that as a result of the expiration pressure it can be raised and clears the flow passage, while the change in the course of the periodically alternating expiration pressure is obtained by placing another ball of a different weight in the recess.

4. Inspiration and expiration apparatus for performing positive expiration pressure (PEP), pursed lips breathing (PLB), oscillating positive expiration pressure (OPEP), incentive inspiration (II) and incentive expiration (IE), comprising a handle, a hollow pipe and a channel connectable to a mouthpiece through said hollow pipe and means for periodically alternating expiration pressure with changeable course and, means for infinitely variably regulating inspiration and expiration pressure, wherein the means for periodically alternating expiration pressure comprises an element for shutting off a flow passage for the air through the channel, said element being acted on by a force of gravity in the direction of the flow passage and being acted on in an opposite direction by expiration pressure, said expiration pressure depending on the supply of air allowed through thereby being variable, said expiration pressure resulting in an up and down movement of the element so that the flow passage is shut off and re-opened in rapid succession during the same exhalation, means for changing the course of the periodically alternating expiration pressure thus obtained, said means for changing comprising replacing the element by another of a different weight, and wherein the means for regulating the inspiration and expiration pressure comprises a rotary control mechanism, a flow aperture for air, said rotary control mechanism infinitely variably increasing the channel or reducing the channel through said hollow pipe (until the channel is shut off) according to a direction of rotation of the rotary control mechanism, said rotary control mechanism being fixed on an outside wall of the apparatus and connected to a shaft fixed on the regulating means.

5. The apparatus of claim 4, wherein the rotary control mechanism comprises a rotary part having a shape of a segment of an ellipsoid obtained by cutting away a piece up to an axis of symmetry in a lengthwise direction, and cutting along two different planes of symmetry in the lengthwise direction, said rotary part lies rotatably enclosed in a space formed as a widening of the channel which permits only rotation, as a result of which the size of the flow passage is regulated infinitely variably, and a narrow groove at right angles in one of the cut faces of the regulating part which narrow groove forms the end of the control path, just before the shutting off of the flow passage, and makes up the only further, still regulatable flow passage for the air, so that a fine adjustment is possible.

6. The apparatus of claim 4 wherein the rotary control mechanism comprises a rotary part having a shape of a cylinder in which there is a U-shaped recess, provided in a transverse direction and at right angles to an axis of symmetry of the cylinder, said U-shaped recess being provided with a narrow groove in a center of a flat base of said recess, at right angles therein, said part being rotatably enclosed in a space which is made as a widening of the channel which permits only rotation, so that the size of the flow passage is regulated, and at the end of the regulating path, just before the flow passage is shut off, the narrow groove acts as the sole, further adjustable flow passage for the air, so that a finer adjustment is possible.

7. Inspiration and expiration apparatus for performing positive expiration pressure (PEP), pursed lips breathing (PLB), oscillating positive expiration pressure (OPEP), incentive inspiration (II) and incentive expiration (IE), comprising a handle, a hollow pipe and a channel connectable to a mouthpiece through said hollow pipe and means for periodically alternating expiration pressure with changeable course and, means for infinitely variably regulating inspiration or expiration pressure, wherein the means for periodically alternating expiration pressure comprises an element for shutting off a flow passage for the air through the channel, said element being acted on by a force of gravity in the direction of the flow passage and being acted on in an opposite direction by expiration pressure, said expiration pressure depending on the supply of air allowed through thereby being variable, said expiration pressure resulting in an up and down movement of the element so that the flow passage is shut off and re-opened in rapid succession during the same exhalation, means for changing the course of the periodically alternating expiration pressure thus obtained, said means for changing comprising replacing the element by another of a different weight, said apparatus further comprising an elongated, cylindrical base part, a bottom end being tapered to form a handgrip, and a top end being provided with a symmetrical, cylindrical recess with a centrally situated lowest point, and wherein the channel runs through a solid part of said base part and is tubular, the channel at one side opening out vertically into a lowest point of the cylindrical recess, and at another side opening out into a side wall, not necessarily horizontally, with a cylindrical widening and a projecting edge running through further as a prolongation to receive a cylindrical end of a hollow pipe having a mouthpiece on an opposite end, wherein the means for periodically alternating pressure comprises at least two cups with lids, inside with a spherical ball rests, having a different weight for each cup, said cups having a shape similar to the cylindrical recess for fitting into the recess in the base part, and in a lowest point of a bottom said cup having a bottom aperture which comes to rest just above an outlet aperture of the channel, and is at least the same size as the channel, and in which each lid is provided with an aperture towards the outside, said lid aperture being at least as large as the bottom aperture, while each ball lying on the bottom of the cup comprises means for shutting of the flow passage for air and has a weight such that the expiration pressure raises each ball and clears the flow passage, means for changing the course of the periodically alternating expiration pressure comprising pushing another cup containing a ball of a different weight into the recess.

* * * * *